United States Patent
Belliere-Baca et al.

(10) Patent No.: US 11,242,316 B2
(45) Date of Patent: Feb. 8, 2022

(54) METHOD FOR MANUFACTURING 2-HYDROXY-4-(METHYLTHIO)BUTYRIC ACID

(71) Applicant: ADISSEO FRANCE S.A.S., Antony (FR)

(72) Inventors: Virginie Belliere-Baca, Millery (FR); Didier Morvan, Mornant (FR)

(73) Assignee: ADISSEO FRANCE S.A.S., Antony (FR)

(*) Notice: Subject to any disclaimer, the term of this patent is extended or adjusted under 35 U.S.C. 154(b) by 51 days.

(21) Appl. No.: 16/624,323

(22) PCT Filed: Mar. 9, 2018

(86) PCT No.: PCT/FR2018/050550
§ 371 (c)(1),
(2) Date: Dec. 19, 2019

(87) PCT Pub. No.: WO2018/167405
PCT Pub. Date: Sep. 20, 2018

(65) Prior Publication Data
US 2021/0188769 A1 Jun. 24, 2021

(30) Foreign Application Priority Data
Mar. 16, 2017 (FR) ...................... 17/52163

(51) Int. Cl.
*C07C 319/12* (2006.01)
*C07C 319/28* (2006.01)
*C07C 323/52* (2006.01)

(52) U.S. Cl.
CPC ......... *C07C 323/52* (2013.01); *C07C 319/12* (2013.01); *C07C 319/28* (2013.01)

(58) Field of Classification Search
CPC ............................. C07C 319/12; C07C 319/28
See application file for complete search history.

(56) References Cited

U.S. PATENT DOCUMENTS

| | | |
|---|---|---|
| 4,524,077 A | 6/1985 | Ruest et al. |
| 4,912,257 A | 3/1990 | Hernandez et al. |
| 5,064,539 A | 11/1991 | Tanimura et al. |
| 6,136,198 A | 10/2000 | Adam et al. |
| 6,375,839 B1 | 4/2002 | Adam et al. |
| 6,413,419 B1 | 7/2002 | Adam et al. |
| 6,712,973 B2 | 3/2004 | Adam et al. |
| 6,743,946 B1 | 6/2004 | Carencotte et al. |
| 7,479,228 B2 | 1/2009 | Schramm et al. |
| 2007/0213560 A1* | 9/2007 | Haga ............... C07C 319/20 562/581 |
| 2017/0369434 A1* | 12/2017 | Mahoney ............ C07C 31/02 |

FOREIGN PATENT DOCUMENTS

| | | | |
|---|---|---|---|
| CN | 104177280 | * 12/2014 | |
| CN | 104262216 A | 1/2015 | |
| CN | 105130861 | * 12/2015 | ........... C07C 319/28 |
| CN | 106432018 A | 2/2017 | |
| EP | 0342629 A1 | 11/1989 | |
| EP | 0739870 A1 | 10/1996 | |
| FR | 2889077 A1 | 2/2007 | |
| JP | 2007238555 A | * 9/2007 | ........... C07C 319/20 |
| JP | 2007238555 A | 9/2007 | |
| WO | 0002852 A1 | 1/2000 | |
| WO | 0002853 A1 | 1/2000 | |
| WO | 2008049927 A1 | 5/2008 | |

OTHER PUBLICATIONS

Thomas (High Performance Liquid Chromatography (HPLC)-Methods, Benefits and Applications, Apr. 2013, pp. 1-6).*
Curran ("Strategy-Level Separations in Organic Synthesis: From Planning to Practice", Angewandte Chemie, Int. Ed., 1998, vol. 37, pp. 1174-1196).*
Bristol Meyers Squibb ("Simulated Moving Bed Chromatography: A Powerful Unit Operation", Pharmaceutical Technology, Oct. 2007, vol. 2007 Supplement, Issue 5, pp. 1-6).*
Kwangnarn LEE "Two-Section Simulated Moving-Bed Process", Separation Science and Technology, 2000, vol. 35, No. 4, pp. 519-534.
Ziyang ZHANG et al. "PowerFeed operation of simulated moving bed units: changing flow-rates during the switching interval", Journal of Chromatography A, 2003, vol. 1006, pp. 87-99.
International Search Report dated Jun. 12, 2018 re: Application No. PCT/FR2018/050550, pp. 1-2, citing: U.S. Pat. No. 4,912,257 A.
Written Opinion dated Jun. 12, 2018 re: Application No. PCT/FR2018/050550, pp. 1-4, citing: U.S. Pat. No. 4,912,257 A.

* cited by examiner

*Primary Examiner* — Rosalynd A Keys
(74) *Attorney, Agent, or Firm* — Cantor Colburn LLP

(57) ABSTRACT

A method for manufacturing 2-hydroxy-4-(methylthio)butyric acid (HMTBA) from 2-hydroxy-4-methylthio-butyronitrile (HMTBN), where HMTBN is hydrolyzed into HMTBA in the presence of a mineral acid in an aqueous medium, the medium is neutralized by addition of a base, a first phase including at least HMTBA and salts and a second phase containing salts are separated, the method including the separation of the HMTBA from the salts of the first phase, by subjecting the latter to a chromatography.

15 Claims, 3 Drawing Sheets

METHOD FOR MANUFACTURING 2-HYDROXY-4-(METHYLTHIO)BUTYRIC ACID

TECHNICAL FIELD

The present disclosure concerns an improved method for preparing 2-hydroxy-4-(methylthio)butyric acid (HMTBA) and a selenium homologue thereof, 2-hydroxy-4-(methylseleno)butyric acid. More particularly, this method incorporates a high-performance step of purifying the obtained HMTBA by acid hydrolysis of 2-hydroxy-4-methylthio-butyronitrile (HMTBN).

BACKGROUND 2-hydroxy-4-(methylthio)butyric acid (HMTBA) and its analogs such as the salts, the chelates, in particular metal chelates (of Zn, Ca, Mn, Mg, Cu, Na, . . . ) and the esters of these acids, such as the isopropylic and tertiobutylic esters of HMTBA, are widely used in animal nutrition. The selenium derivatives of these hydroxyl analogs of methionine are also constituents of major interest in animal nutrition.

The preparation of HMTBA may be operated by various direct or indirect HMTBN hydrolysis methods. This hydrolysis is conventionally carried out by a mineral acid such as hydrochloric acid or sulfuric acid, it may also be carried out by enzymatic hydrolysis.

Thus, WO 00/02852A1 describes the manufacture of HMTBA by hydrolysis of HMTBN with sulfuric acid in two steps. According to a first step [1], there is carried out a hydration reaction of 2-hydroxy-4-methylthio-butyronitrile (HMTBN) into 2-hydroxy-4-methylthio-butyramide (HMTBM) which is thereafter hydrolyzed in a second step [2] into 2-hydroxy-4-(methylthio)butyric acid (HMTBA), as represented by the reactions below:

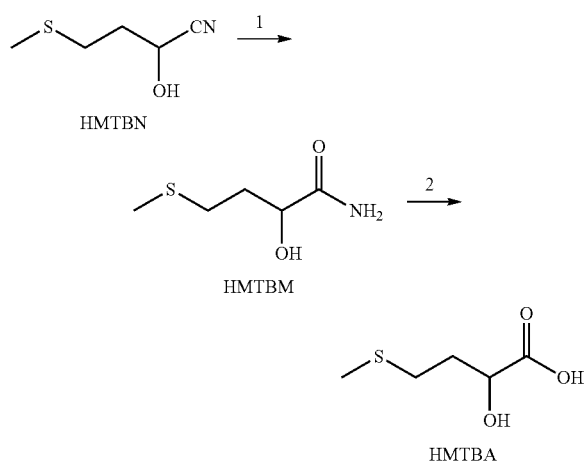

The obtained mixture containing HMTBA can thereafter be treated through one or several purification step(s) as described in the documents WO 00/02853A1, U.S. Pat. Nos. 4,524,077A, 4,912,257A or JP 2007238555A.

Thus, according to U.S. Pat. No. 4,524,077A, there is carried out a direct extraction of the hydrolysis medium by a water immiscible solvent, followed by an evaporation of said solvent in the presence of an amount of water so as to reduce the apparition of a brown color of the obtained product. The solvent is selected in particular from methyl ethyl ketone, methyl isobutyl ketone, methyl tert-butyl ether, diisopropyl ether and diethyl carbonate. The salting out of a saline aqueous phase is then observed. The solvent is removed from the organic phase by evaporation and the final HMTBA solution is adapted to the commercial titer by water addition.

U.S. Pat. No. 4,912,257A describes, following the steps of hydrolysis of HMTBN in the presence of sulfuric acid and neutralization of the reaction medium by ammonia, a step of separating an organic phase containing HMTBA and remaining salts and an aqueous phase containing salts, essentially ammonium sulfate and traces of HMTBA, on the one hand, the organic phase being thereafter concentrated then filtered to recover the HMTBA, and on the other hand, the aqueous phase being concentrated and then the salts are precipitated. Bringing the HMTBA thus obtained to the final titer is performed by water addition.

Finally, the document JP 2007238555A proposes carrying out, after the hydrolysis step but before the neutralization step, a distillation to remove light molecules, predominantly containing sulfur and formic acid. This distillation is operated at temperatures between 80° C. and 120° C. and at pressures between 0.5 and 1.5 bar. A biphasic separation into two organic and aqueous phases is then performed as in the previous documents and the two phases also treated in the same way.

The synthesis of 2-hydroxy-4-(methylseleno)butyric acid is also known. It may in particular be manufactured by acid hydrolysis of 2-hydroxy-4-methylseleno-butyronitrile as described in WO 2008/049927A1.

Regardless of the technique for separating the aforementioned acids from the salts resulting from the neutralization, these salts, and specifically ammonium sulfate, can be recovered and particularly commercialized as such or after one or more complementary purification treatment(s).

Nonetheless, the known methods such as those presented above suffer from multiple drawbacks resulting from the technique of isolating the final product HMTBA. They are summarized hereinafter:

a) The unavoidable presence of 1 to 2 weight % of ammonium sulfate, affecting the quality of HMTBA and which in the final product, substitutes water. Indeed, this lower presence of water induces, by equilibrium thermodynamic laws, a higher concentration of oligomers of HMTBA in the final product. This generates a higher viscosity of the final product and limits its acidity;

b) A dark brown color and an unpleasant odor;

c) High operating cost due to the reliability and maintenance of the filtration steps;

d) High cost of the final product due to the use of means such as the extraction with solvents.

BRIEF SUMMARY

The method of the disclosure allows overcoming all these drawbacks thanks to the implementation of an HMTBA isolation step that can substitute the existing one(s), this isolation being carried out by chromatography of an HMTBA flow coming from the hydrolysis and neutralization reaction medium.

Thus, the disclosure provides a method for manufacturing HMTBA from HMTBN, comprising the following steps:

HMTBN is hydrolyzed into HMTBA in the presence of a mineral acid in an aqueous medium, Said medium is neutralized by addition of a base, A first phase comprising at least HMTBA and salts and a second phase containing salts are separated, Said method comprising a step according to which the separation of the HMTBA from said salts of the first phase is carried out by subjecting the latter to a chromatography.

Chromatography according to the disclosure means any separative method which allows separating a phase comprising at least HMTBA and salts into two phases, one enriched in HMTBA and the other enriched in salts. Such a method implements a stationary phase and a mobile phase. As examples, it may be carried out in a static or non-static bed in one or several column(s) such as the chromatography systems of at least two columns described in FR2889077 or in the article *Separation Science and Technology* 35(4):519-534, 2000, or the chromatography systems of at least three columns such as the iSMB technologies as described in EP 0342629 and U.S. Pat. No. 5,064,539), SSMB, AMB, VARICOL™ (as described in U.S. Pat. Nos. 6,136,198, 6,375,839, 6,413,419 and 6,712,973), MODICON™ (as described in U.S. Pat. No. 7,479,228), POWERFEED™ (as described in U.S. Pat. No. 5,102,553 and the article «*Power Feed operation of simulated moving bed units: changing flow-rates during the switching interval*», Zhang et al. in *Journal of Chromatography A*, 1006:87-99, 2003), or MCSGP (Multicolumn Countercurrent Solvent Gradient Purification).

It has been found that it is possible to remove salts very efficiently from a flow containing HMTBA by chromatography which involves a double exclusion effect both steric and ionic. As an indication, the use of this chromatography step allows separating 95% of the ammonium sulfate contained in the first phase thus treated.

Chromatography is advantageously carried out by treating the first phase containing HMTBA on a resin. The resin may be an anionic or cationic resin.

If the resin is anionic, it is preferably charged with anions selected from $OH^-$, $Cl^-$, $SO_4^{2-}$.

If it is cationic, it is preferably charged with cations selected from $NH_4^+$, $H^+$, $Na^+$, $K^+$ and $Ca^{2+}$.

Advantageously, the chromatography is performed in a Sequential Simulated Moving Bed (SSMB). By difference in affinity between the liquid phase consisting of an aqueous solution of HMTBA and the solid of the column, this technique allows separating the mineral salts, herein the ammonium sulfate, from the organic species, herein predominantly HMTBA. In addition to its efficiency, this separation requires no addition of other reagent and does not result in the formation of any additional salt. Another advantage to this technology is the ease of operation and the long life of the columns.

The flow of HMTBA that is treated in the context of the method of the disclosure therefore comes from the neutralization medium. According to one variant, the neutralization step may be preceded by a distillation step as mentioned above with reference to document JP 2007238555A, and in particular under conditions of temperature from 80° C. to 120° C. and of pressure from 0.5 to 1.5 bar. The treated HMTBA flow contains predominantly HMTBA. It may contain water, salts, impurities and sub-products, in particular organic ones such as functionalized hydroxybutyrolactones and methylthiopropionic aldehyde (MMP). Preferably, the concentration of HMTBA of the flow to be treated by chromatography is 30 to 90% (m/m), or even 50 to 80% (m/m). If necessary, it is adjusted by water addition.

In a preferred version, the eluent of the chromatography is an aqueous solvent. It is advantageously selected from water, water being pure or resulting from recycling, and mixtures thereof with one or more organic solvent(s). The latter are preferably selected from alcohols, such as methanol and ethanol, furans such as tetrahydrofuran, and acetonitrile.

According to a variant of the disclosure, the aqueous solvent is selected from water, an acidic aqueous solution and a basic aqueous solution. It falls within the general competence and knowledge of the those skilled in the art to select the acid or the base, as well as their concentration, according to the flow of HMTBA, bearing in mind that in an implementation on an industrial scale the most economical solutions will be retained.

Advantageously, the chromatography is carried out under conditions of elution rate that those skilled in the art will determine in view of their general knowledge.

In a particular implementation of the separation step, the chromatography is performed according to a simulated moving bed mode (SMB) or according to a sequential simulated moving bed mode (SSMB).

Although the separation step described above is suitable for any flow of HMTBA, in a preferred embodiment, it is separated from ammonium sulfate salts $NH_4HSO_4$ or $(NH_4)_2HSO_4$ and mixtures thereof, resulting from a hydrolysis of HMTBA in the presence of sulfuric acid then neutralization by addition of ammonia or ammonium hydroxide.

Any additional step for the HMTBA purification purposes may be incorporated into the method at any stage thereof. Thus, as previously indicated, a step of distilling the hydrolysis medium, for stripping the light molecules, before neutralization, may be provided. Also, according to a very advantageous implementation of the method of the disclosure, the aforementioned step of separation by chromatography is carried out on an HMTBA flow which results from a separation step, by decantation, of the first phase comprising at least HMTBA and salts and of the second phase containing salts. The separation efficiency is, under these conditions, much higher and the service life of the chromatography columns is considerably increased. Any other technique for separating these two phases, such as centrifugation or liquid/liquid separation, may be used where it does not involve extraction with solvents. It extraordinarily facilitates the subsequent processes of purification and total recovery of HMTBA, on the one hand, and ammonium sulfate, on the other hand, with high yield and efficiency. Thus, separation techniques of the extraction type involving a water immiscible solvent are not necessary or even counterproductive; they do not substantially improve the quality or yield, increase the cost of the method and complicate the installation.

At the end of the separation step by chromatography, a phase rich in HMTBA and a phase rich in salts are recovered. One or both can be subjected to evaporation and the resulting aqueous solvent is recycled to at least any one of the steps of said method.

At the output of the chromatography column, the HMTBA is then brought back to the initial titer by evaporation of the excess water supplied during the separation on said column. This improvement in the HMTBA manufacturing method allows increasing the quality of the final product as well as facilitating the operation.

The obtained product is a diluted HMTBA which will be brought back to a titer of up to 95%, during an evaporation step. The water removed from the HMTBA will advantageously be reintroduced into the method at the chromatographic separation step or elsewhere. The phase containing the ammonium sulfate may be reintroduced at the neutralization step or elsewhere.

The rest of the method remaining identical.

This separation may also be used to advantageously separate the sulfur species other than HMTBA in order to improve the quality of the final product. The phases containing HMTBA and ammonium sulfate will be treated in the same manner as described above, the new phase containing sulfur products will then be separated and treated suitably.

The disclosure also concerns 2-hydroxy-4-(methylthio) butyric acid obtained according to the method above, in which the level of oligomers is reduced relative to the HMTBA obtained according to a method of the prior art and whose salts proportion is at most 0.8% (w/w), or even at most 0.5% and even at most 0.3%, and even salts only in the form of traces.

BRIEF DESCRIPTION OF THE DRAWINGS

The present disclosure will be more fully described and its advantages with respect to the state of the art will emerge from the examples illustrating the manufacture of HMTBA according to a method of the disclosure, on the industrial scale, and in support to the enclosed FIGS. 1-4 according to which.

DETAILED DESCRIPTION AND EXAMPLES

This example is of course not limiting both with regards to the conditions of implementation and with regards to the obtained compound, which according to the disclosure may also be 2-hydroxy-4-(methylseleno)butyric acid.

Example: Manufacture of HMTBA from HMTBN, According to the Disclosure

Figure 1:
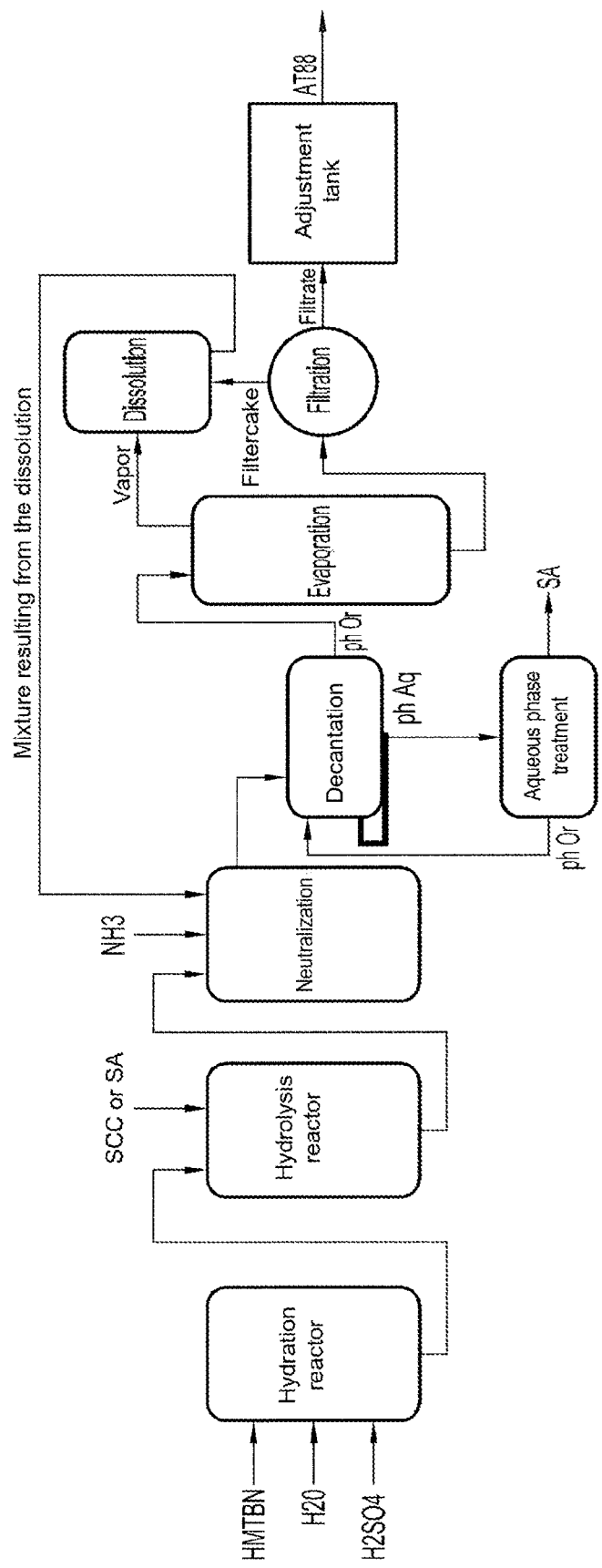
FIG. 1 is a diagram of a known industrial method for manufacturing HMTBA.
Figure 2:
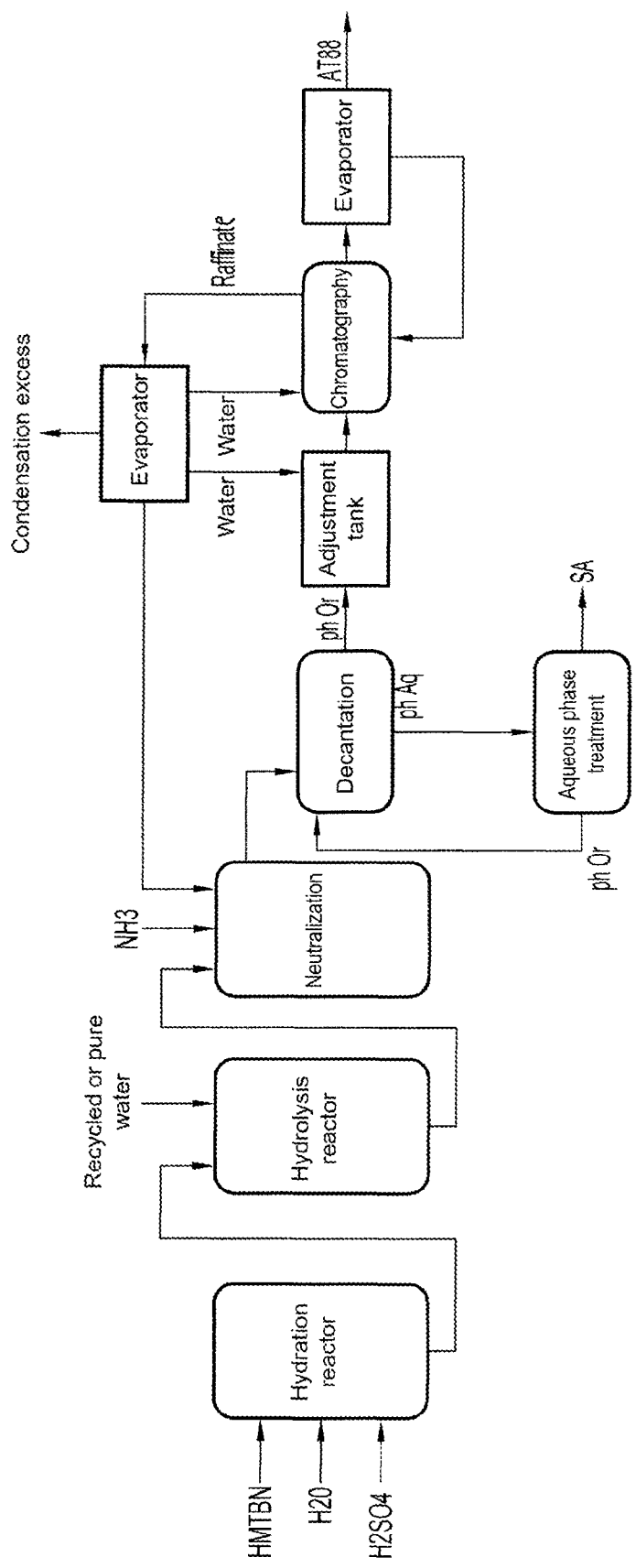
FIG. 2 is a diagram of a method for manufacturing HMTBA, according to the disclosure, on an industrial scale.

The following method is illustrated in FIG. 2. It may be compared with FIG. 1 corresponding to a conventional method for synthesizing HMTBA.

1) Synthesis of HMTBN

HMTBN is synthesized according to a method which is a variant of that disclosed in the document EP 0739870A1 described for the synthesis of the amino acid DL-methionine. It differs only in the nitrile synthesis reagent, which according to the present example is ammonia-free water, while according to the document, the reagent is an aqueous ammonia solution. This manufacture is well known to the those skilled in the art.

2) Synthesis of the HMTBA 2.1) Hydrolysis of HMTBN

The product resulting from the above synthesis step is brought into contact with concentrated sulfuric acid, preferably at 98%, in an acidification loop where the product and the acid are mixed together. In order to avoid local heat-ups leading to the destruction of the nitrile and the formation of side reactions causing an increase in coloration, the acidification is carried out continuously with a large recirculation, by adding the concentrated sulfuric acid to the acidified solution of nitrile, this solution preferably having a concentration of 20-50% by weight of acid.

Since it is necessary to remove the heat of dilution of the sulfuric acid, the acidification loop is provided with one or several heat exchanger(s) such that the temperature of the reaction does not exceed 65° C.

The sulfuric acid/HMTBN molar ratio is comprised between 0.8-1.5. The proportion of water is adjusted such that the acidified solution is constituted by one single phase and is capable of maintaining in solution the ammonium sulfate that will be formed during the hydrolysis reaction and during the neutralization with the following ammonium hydroxide.

After a contact time of 30-60 minutes, water is added until a concentration of 20% is obtained at the end of the hydrolysis step. The reaction medium obtained is heated to a temperature comprised between 110 and 130° C., the stay time is comprised between 2 hours and 4 hours to obtain the HMTBA.

Throughout the course of the hydrolysis, it is necessary to apply to the reactor a slight vacuum (between about 20 and 200 mm) so as to remove the small excess of HCN used in the synthesis of HMTBN, as well as the volatile impurities that might be formed in the reaction and to which the unpleasant odor of the final product is attributed.

2.2) Neutralization of the Hydrolysis Medium

The hydrolysis reaction mixture is cooled down to 50-70° C., and its excess acid is neutralized with an ammonia solution of 20-35 weight %, said solution possibly being formed in situ by bubbling gaseous $NH_3$. Said neutralization may require a cooling in order not to exceed the temperature of 90° C.

3) Purification of HMTBA 3.1) Prior Separation Steps

The obtained neutralized mass comprises two phases which have distinctly different densities and can be easily decanted. They consist of a first phase which contains 93-95% of the formed HMTBA and a second phase which contains the rest. The ammonium sulfate formed during the hydrolysis reaction and the neutralization of the acid used in excess, is distributed between the two phases, the second phase being the richest one with 70-75 weight %.

From the second phase, the ammonium sulfate is precipitated by evaporation of water at atmospheric pressure or under reduced pressure. The resulting solid is separated by any standard solid-liquid separation method such as filtration and/or centrifugation, and the resulting liquid containing the portion of the ammonium sulfate that has not precipitated and the HMTBA, is recycled into the neutralization vessel. This method allows obtaining ammonium sulfate which, when dried, has a high purity and is substantially free of HMTBA; the latter is recovered in its entirety by recycling at the head of the separation process, while remaining incorporated in the first phase.

3.2) Chromatography Separation Step According to the Disclosure

The first phase coming from the decanter and containing the HMTBA of both flows (neutralization and recycling) is led to an adjustment tank to perform a dilution before purification on a chromatographic column. In normal operation, 800 t per day of first phase are treated and in the context of the disclosure this phase is diluted with 240 t per day of recycled water coming from the post-purification evaporation on a chromatographic column. This first phase contains in particular and before dilution, 65% w/w of HMTBA, 14% w/w of ammonium sulfate predominantly in its form $(NH_4)_2SO_4$.

Figure 3:
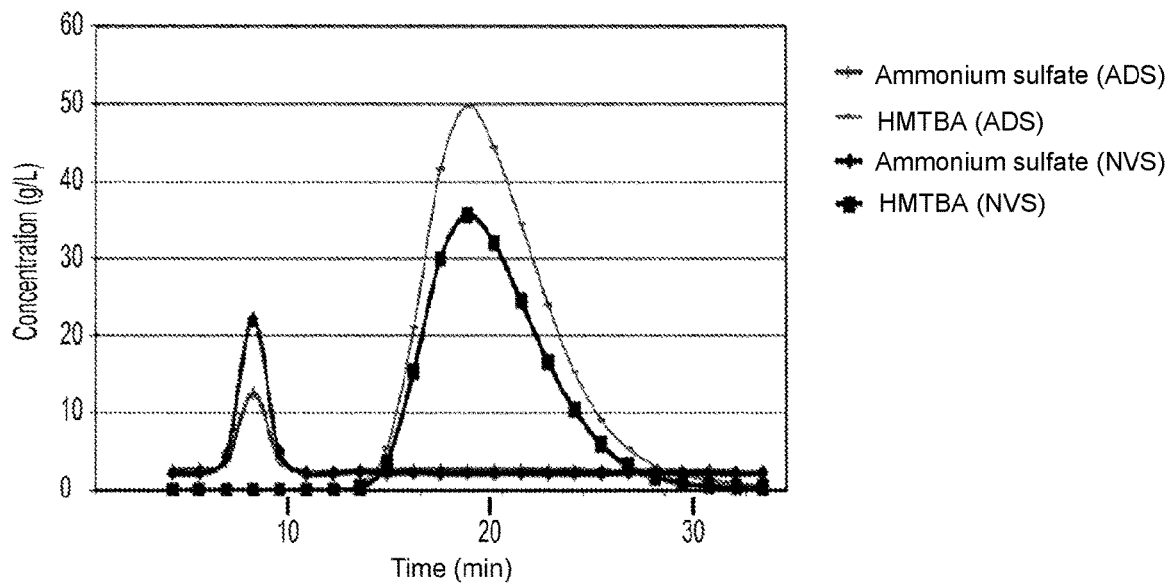
FIG. 3 is a graphical representation of the separation between ammonium sulfate and HMTBA.

Afterwards, the first diluted phase is conveyed on a chromatography column of the simulated moving bed technology for purification. The used eluent is recycled water coming from the post-purification evaporation. 3700 t per day of water are thus used for purification of the first phase which represents 1040 t per day after the dilution step. The separation is performed in the column by size and ion exclusion between the liquid phase and the solid phase of the column. The separation between ammonium sulfate and HMTBA is represented in FIG. 3, in which HMTBA is represented under the name «Organic» and ammonium sulfate under the name «Salt». The acronyms ADS and NVS represent liquid chromatography analyses performed on two different sites for confirmation of the results.

The separation between ammonium sulfate and HMTBA is up to 95%. In other words, 95% of the ammonium sulfate contained in the first phase are separated by the simulated moving bed technology.

Figure 4:
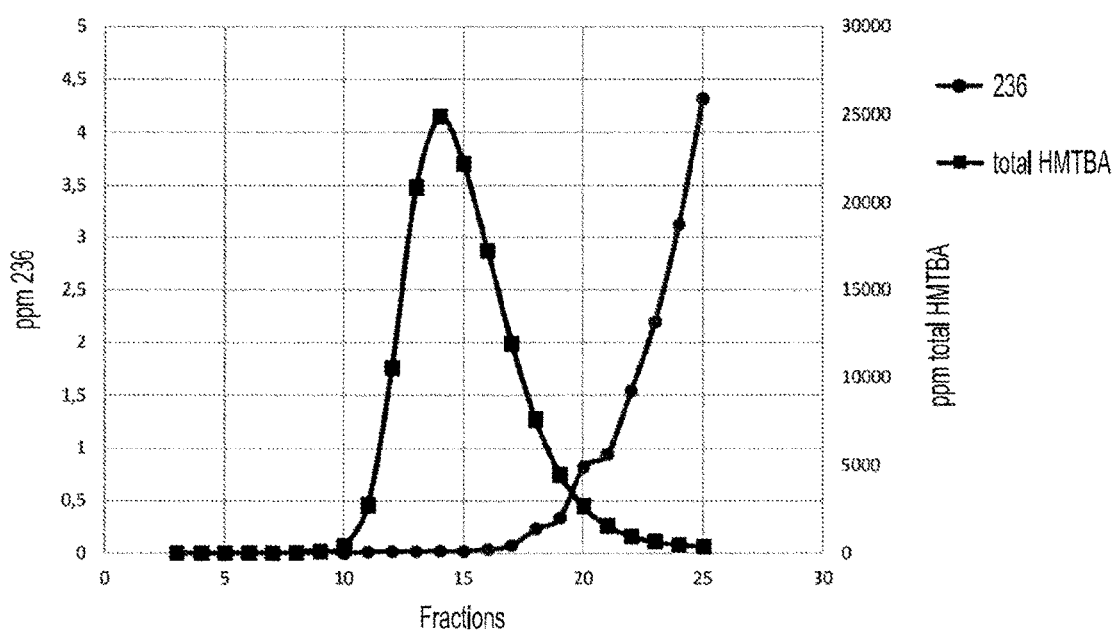
FIG. 4 is a graphical representation of the separation of functionalized hydroxybutyrolactones.

This separation on a chromatographic column allows, furthermore, the possibility of separating an organic major impurity contained in the first phase. This impurity, called MW236, is a functionalized hydroxybutyrolactone. The graphical representation of this separation is given in FIG. 4.

80% w/w of this impurity can be removed from the first phase by this separative technology.

It emerges from this example that the purification step by chromatography can replace at least one or even all of the separation steps conventionally performed, as highlighted by the comparison of FIGS. 1 and 2, and that it allows obtaining a HMTBA, almost free of salts, and containing less oligomers and impurities in particular organic impurities such as functionalized hydroxybutyrolactones and MMP.

The separation of the species is not limited to these examples.

The following examples illustrate the purification step of the method of the disclosure carried out on HMTBA flows other than that of the preceding example.

At the output of the chromatography column, two main flows are obtained, a first one representing 1140 t per day and containing 95% of the ammonium sulfate contained in the first initial phase and a second one representing 3600 t per day of an HMTBA rich phase. The ammonium sulfate rich phase is called raffinate. Both phases are then conveyed towards the evaporators for concentration and recovery of water for recycling.

The ammonium sulfate rich phase, called raffinate, is conveyed towards an evaporator for concentration and recovery of water for recirculation in the method. A mechanical compression evaporator is used but any evaporator technology known to those skilled in the art can be advantageously used at this step of the method.

The water recovered at this step is redistributed at two locations in the process. A first flow representing 655 t per day of water is recycled to the chromatography and used as an eluent and a second flow representing 240 t per day of water, used in the first phase dilution step.

The phase concentrated in ammonium sulfate, which represents 125 t per day, is recycled to the neutralization step of the method.

An excess condensate, representing 105 t per day, is removed from the system at this step.

The HMTBA rich phase resulting from the chromatography step is also condensed by mechanical compression evaporator or any appropriate evaporation technology known to those skilled in the art. The water recovered by evaporation is recycled in the method at the chromatography step and serves as an eluent. This water represents 3020 t per day.

This evaporation also allows obtaining an HMTBA rich phase which is advantageously concentrated to 88% w/w of HMTBA to directly obtain the final product, called AT88. This AT88 product flow represents 560 t per day. Typically, this final product contains (in w/w): 88% of HMTBA and oligomeric derivatives thereof, 11.2% of water, 0.8% of ammonium sulfate and traces of other organic products.

The following table shows the effectiveness of a method of the disclosure compared to a known method, from a same flow of the first phase at the output of the decantation at a flow rate of 33 300 kg/h, giving the composition of the final product:

TABLE

| % | Method of the disclosure | Known method |
|---|---|---|
| HMTBA | 88 | 88 |
| Water | 11.2 | 10 |
| $(NH_4)_2SO_4$ | 0.8 | 1.6 |
| Functionalized hydroxybutyrolactones | 0 | 0.5 |
| MMP | 0 | 0.08 |

Thanks to the method of the disclosure, there is obtained HMTBA in which the remaining proportion of salts is decreased by half and in which organic impurities are no longer detected.

The invention claimed is:

1. A method for manufacturing 2-hydroxy-4-(methylthio)butyric acid (HMTBA) from 2-hydroxy-4-methylthio-butyronitrile (HMTBN), comprising the following steps:
   HMTBN is hydrolyzed into HMTBA in the presence of a mineral acid in an aqueous medium,
   said medium is neutralized by addition of ammonia or ammonium hydroxide,
   a first phase comprising at least HMTBA and salts and a second phase containing salts are separated,
   said method wherein the separation of the HMTBA from said salts of the first phase, is carried out by subjecting the latter to a chromatography, said chromatography involving both a steric and an ionic exclusion.

2. The manufacturing method according to claim 1, wherein the chromatography is performed by treating the first phase containing HMTBA on a resin.

3. The manufacturing method according to claim 2, wherein the resin is an anionic resin which is charged with anions selected from $OH^-$, $Cl^-$, $SO_4^{2-}$.

4. The manufacturing method according to claim 2, wherein the resin is a cationic resin which is charged with cations selected from $NH_4^+$, $H^+$, $Na^+$, $K^+$ and $Ca^{2+}$.

5. The manufacturing method according to claim 1, wherein the eluent of the chromatography is an aqueous solvent.

6. The manufacturing method according to claim 5, wherein the aqueous solvent is selected from water and mixtures thereof with one or more organic solvent(s) selected from the group consisting of alcohols, furans and acetonitrile.

7. The manufacturing method according to claim 5, wherein the aqueous solvent is selected from water, an acidic aqueous solution and a basic aqueous solution.

8. The manufacturing method according to claim 1, wherein the chromatography is performed according to a simulated moving bed mode (SMB) or according to a sequential simulated moving bed mode (SSMB).

9. The manufacturing method according to claim 1, wherein, before separation, the concentration of HMTBA in the first phase ranges from 30 to 90% (m/m).

10. The manufacturing method according to claim 9, wherein the concentration of HMTBA is adjusted by addition of water.

11. The manufacturing method according to claim 1, wherein the hydrolysis of HMTBN is performed in the presence of sulfuric acid and in that the neutralization is performed by addition of ammonia or ammonium hydroxide.

12. The manufacturing method according to claim 1, wherein, after the hydrolysis of HMTBN and before the neutralization, a distillation is carried out at a temperature of 80° C. to 120° C. and a pressure of 0.5 bar to 1.5 bar.

13. The manufacturing method according to claim 1, wherein the first phase comprising at least HMTBA and salts and the second phase containing salts are separated by decantation.

14. The manufacturing method according to claim 1, wherein the phase rich in HMTBA and/or the phase rich in salts recovered at the end of the chromatography are subjected to evaporation and the resulting aqueous solvent is recycled to at least any one of the steps of said method.

15. The manufacturing method according to claim 6, wherein the organic solvent is an alcohol, then the alcohol is methanol or ethanol, and wherein the organic solvent is a furan, then the furan is tetrahydrofuran.

* * * * *